US00PP18398P2

(12) United States Plant Patent
Horvath

(10) Patent No.: US PP18,398 P2
(45) Date of Patent: Jan. 1, 2008

(54) ***SEDUM TELEPHIUM* PLANT NAMED 'BEKA'**

(50) Latin Name: *Sedum telephium*
Varietal Denomination: Beka

(76) Inventor: Brent Horvath, 10702 Seaman Rd., Hebron, IL (US) 60034

( * ) Notice: Subject to any disclaimer, the term of this patent is extended or adjusted under 35 U.S.C. 154(b) by 0 days.

(21) Appl. No.: 11/440,245

(22) Filed: May 25, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Brent Horvath

(57) ABSTRACT

A new, distinct *Sedum telephium* plant as shown and described, characterized by a thin green edge and chartreuse yellow center to the foliage.

2 Drawing Sheets

Figure 1:
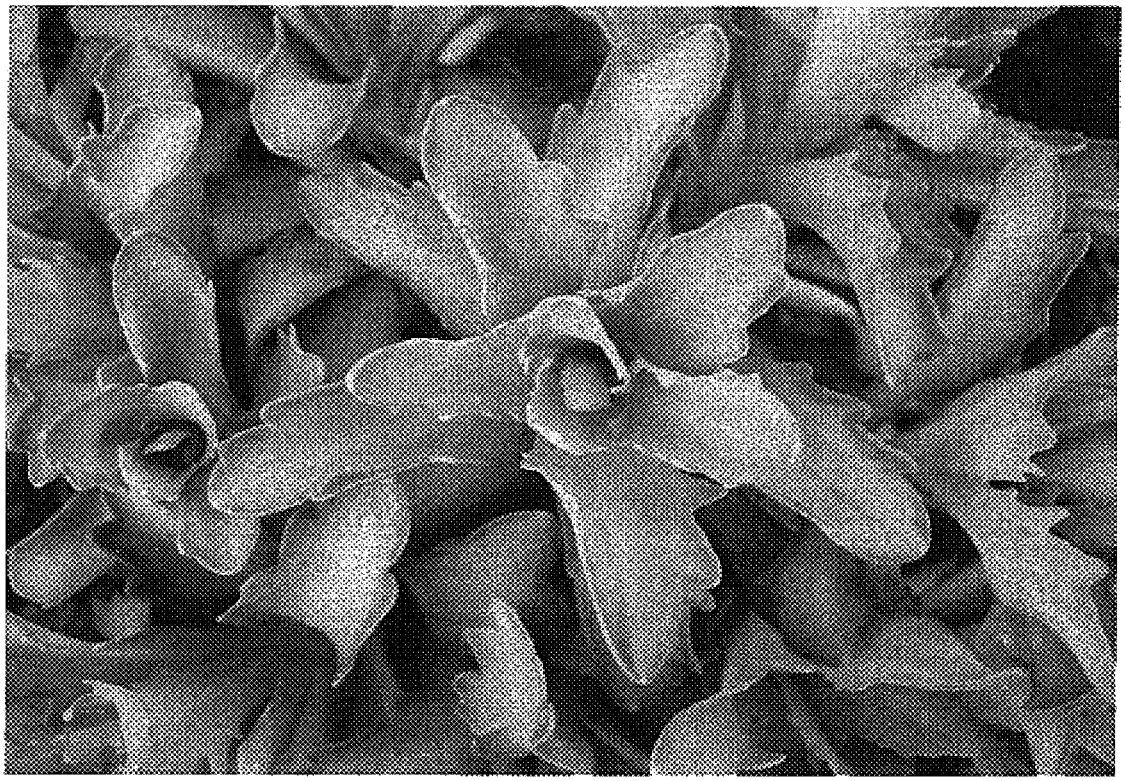

Latin name: *Sedum telephium.*
Cultivar name: 'Beka'.

BACKGROUND OF THE INVENTION

The present invention relates to a new form of *Sedum telephium* plant named 'Beka'. A naturally occurring sport or mutation of *Sedum telephium* 'Lajos' U.S. Plant Pat. No. 14,421 characterized by a thin green edge and chartreuse yellow center to the foliage, compared to yellow edged green centered foliage of *Sedum telephium* 'Lajos'. The parent plant, *Sedum telephium* 'Lajos' is a sport of *Sedum telephium* 'Autumn Joy' of hybrid origin between *Sedum telephium* and *Sedum spectabile.* The new plant was found as a sport by the inventor on a plant of *Sedum telephium* 'Lajos' at a garden in Spring Grove, Ill. in 2000. The selection of this plant was due to its' variegated foliage. Asexual, vegetative tip cutting propagation and division has been the means of reproduction. Propagation has taken place at Intrinsic Perennial Gardens, Inc. Hebron, Ill. since 2001. The new *Sedum* has shown to be stable and identical in reproduction to the parent after rooting over 400 vegetative tip cuttings from 2002 to 2005.

SUMMARY OF THE INVENTION

In the following description, color references are made to The Royal Horticultural Society Colour Chart. The new *Sedum telephium* plant named 'Beka' has shown the characteristic of a thin green edge and chartreuse yellow center to the foliage on a tall upright *Sedum* to be unique and stable. Plants of the new *Sedum* can be compared to plants of *Sedum alboroseum* 'Clown' unpatented also known as 'Medio-Variegatum'. 1. The new *Sedum* is a sport occurring on a hybrid with telephium while the 'Clown' species is alboroseum. 2. The new *Sedum* has a thinner green edge, typically a 2–3 mm wide edge to the leaf while 'Clown' has a broader variegation, typically 4–5 mm wide. 3. The new *Sedum* flower as a whole has a reddish purple flower color 187 D while 'Clown' has a white flower with hints of pink.

Plants of the new *Sedum* can also be compared to its' parent plant of *Sedum telephium* 'Lajos'. 1. The new *sedum* has a thin green edge color 137 A and a chartreuse yellow center color 146 C compared to the yellow edged foliage color 11 C and green center color 137 A.

DESCRIPTION OF PHOTOGRAPHS

FIG. 1. Close up of growing tip in Spring.

Figure 2:
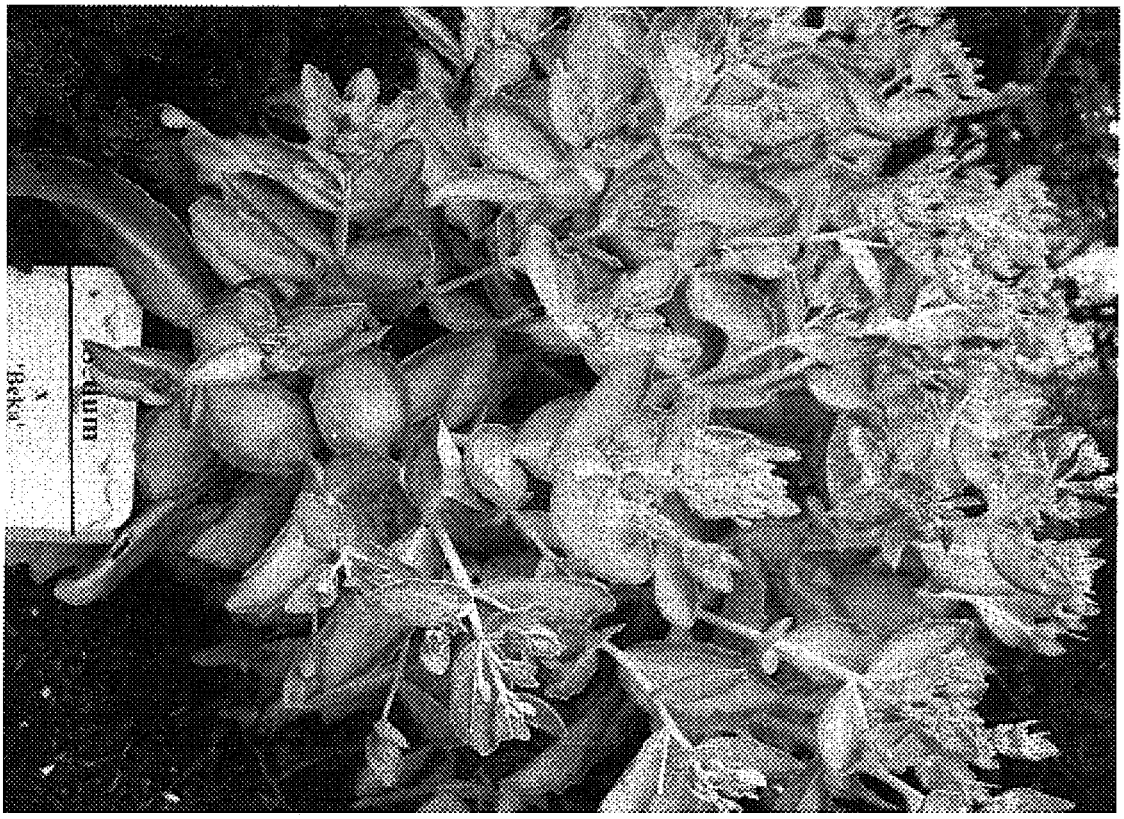

FIG. 2. A clump before budding.

Figure 3:
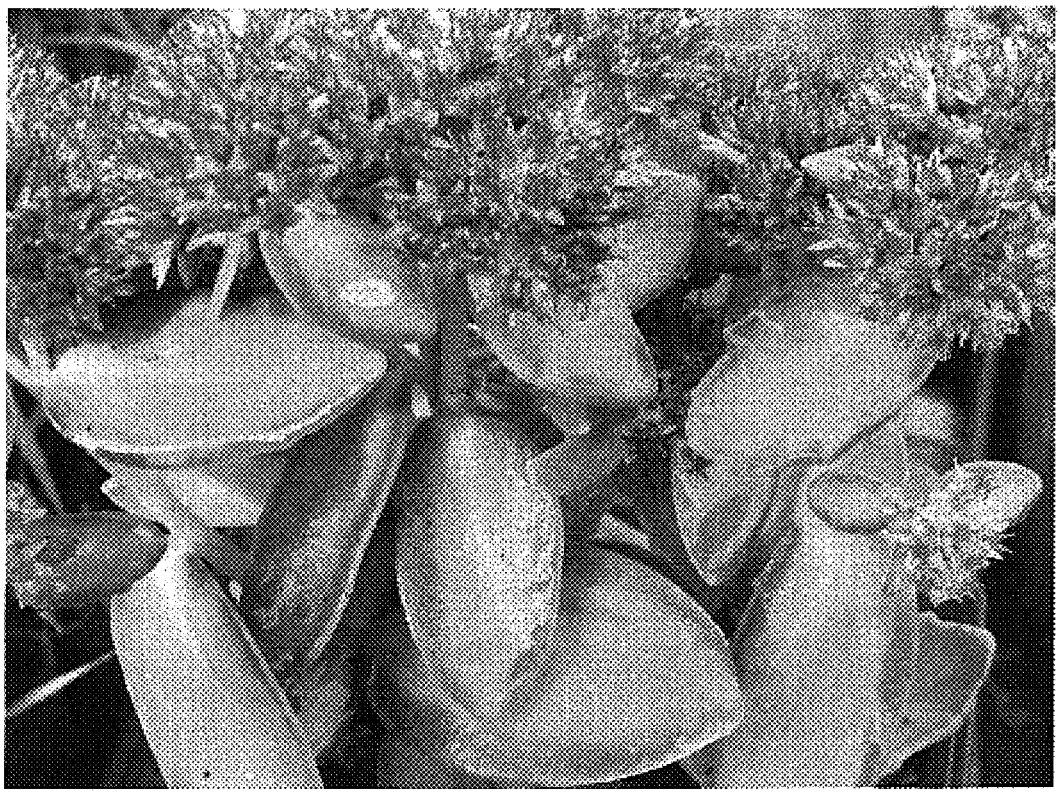

FIG. 3. Close up of flowering plant in Fall.

Figure 4:
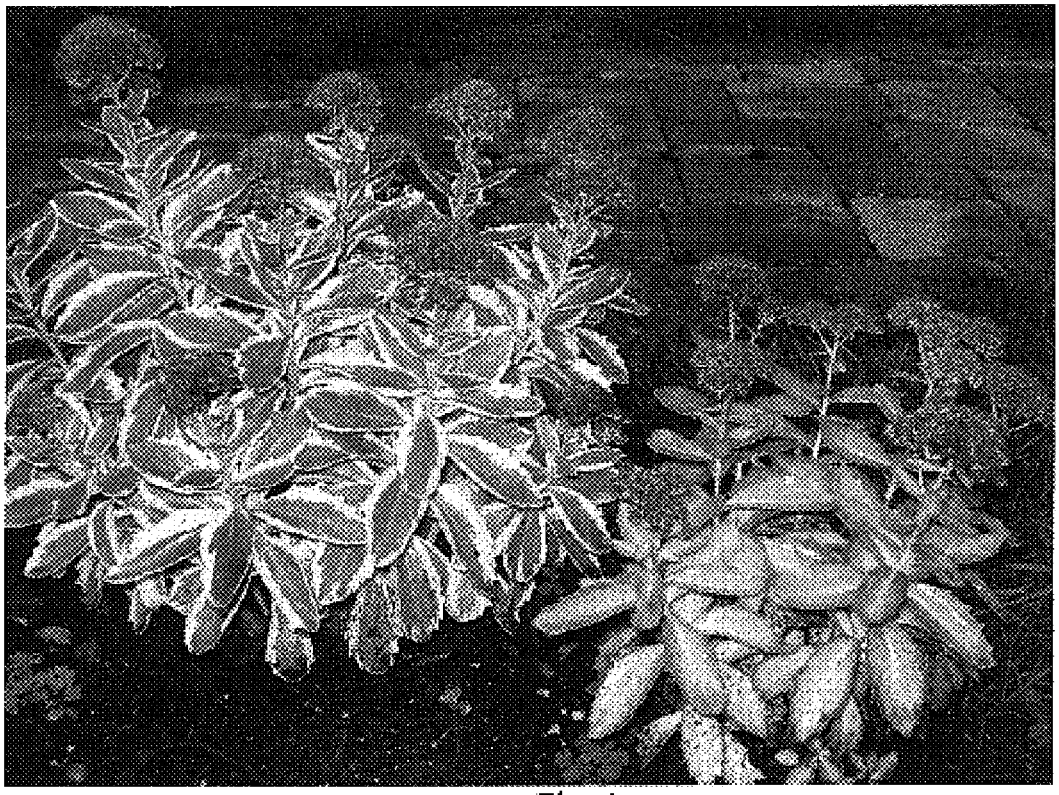

FIG. 4. A picture of parent plant on left and new plant on right.

DETAILED BOTANICAL DESCRIPTION

In the following description, color references are made to The Royal Horticultural Society Colour Chart.

Botanical classification: *Sedum telephium* cultivar 'Beka'.
Parentage: Sport of *Sedum telephium* 'Lajos',
Propagation: Vegetative tip cuttings and division.
Plant description: Overall habit of the new *Sedum* is strongly clumping mounds with upright stems topped by reddish purple flowers in September. Vigor is moderate.
- *Plant height.*—30–45 cm.
- *Plant width.*—30–45 cm.
- *Stem diameter.*—5–12 mm.

Foliage:
- *Type.*—Deciduous.
- *Shape.*—Obovate.
- *Petiole.*—None.
- *Length.*—5–8 cm.
- *Width.*—3–4 cm.
- *Thickness.*—1–2 mm.
- *Margin.*—Coarsely and irregularly toothed.
- *Texture.*—Smooth.
- *Leaf arrangement.*—Alternate, crowded except at the base of the stems.
- *Leaf pattern.*—The typical measurements of the leaf patterns are 2–3 cm wide and 4–7 cm long chartreuse yellow centers vs. typically 2–3 mm of green along the entire edge.
- *Adaxial leaf description.*—The green edge is color 137 A. The center of the adaxial side of the leaf is color 146 C.
- *Abaxial leaf description.*—The green edge is color 137 C. The center of the abaxial side of the leaf is color 146 C.

Flower:

*Petal count.*—5.

*Flower type.*—Panicle.

*Panicle color.*—As a whole the color is 187 D.

*Flower size.*—3 mm across, 5 mm tall.

*Carpel color.*—61 A.

*Sepal size.*—1 mm across, 2 mm tall.

*Sepal color.*—11 C.

*Peduncle color.*—145 B

*Flower number.*—Approximately 2000–3000 per mature panicle measuring 10–15. cm.

*Fertility.*—Sterile, no anthers, no stamens.

*Blooming habit.*—Domed, terminal panicle on up to 45 cm stems.

*Bloom period and duration.*—September into October.

*Scent.*—No scent noticed.

*Bud color.*—158 B.

*Bloom color.*—187 D.

*Fruit.*—none.

*Disease resistance.*—Resistance to diseases common to *Sedum* has not been observed on plants grown under nursery conditions.

I claim:

1. A new, distinct *Sedum telephium* plant as shown and described, characterized by a thin green edge and chartreuse yellow center to the foliage.

* * * * *